(12) United States Patent
Robotti

(10) Patent No.: US 7,384,754 B2
(45) Date of Patent: Jun. 10, 2008

(54) ENRICHMENT AND TAGGING OF GLYCOSYLATED PROTEINS

(75) Inventor: Karla M. Robotti, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 162 days.

(21) Appl. No.: 10/699,449

(22) Filed: Oct. 31, 2003

(65) Prior Publication Data

US 2005/0095647 A1 May 5, 2005

(51) Int. Cl.
*G01N 33/53* (2006.01)
*G01N 33/00* (2006.01)
*C12P 21/06* (2006.01)

(52) U.S. Cl. .................. 435/7.1; 435/68.1; 436/92

(58) Field of Classification Search ............ None
See application file for complete search history.

(56) References Cited

U.S. PATENT DOCUMENTS

2004/0023306 A1* 2/2004 Aebersold et al. ........... 435/7.1
2005/0261475 A1* 11/2005 Tseng et al. ................. 530/333
2006/0141528 A1* 6/2006 Aebersold et al. ........... 435/7.1

OTHER PUBLICATIONS

Garlick et al. Characterization of Glycosylated Hemoglobins. Relevance to monitoring of diabetic control and anlysis of other proteins. J. Clin. Invest. 1983. vol. 71, pp. 1062-1072.*
Klenk et al. Determination of Glycosylated Hemoglobin by Affinity Chromatography: Comparison with Colorimetric and Ion-Exchange Methods, and Effects of Common Interferences. Clin. Chem. 1982, vol. 28, No. 10, pp. 2088-2094.*
Spiro. Mini Review. Protein glycosylation: nature, distribution, enzymatic formation, and disease implications of glycopeptide bonds. Glycobiology, 2002, vol. 12, No. 4, pp. 43R-56R.*
Wells et al. Mapping Sites of 0-GlcNac Modification Using Affinity Tags for Serine and Thronine Post-translational Modifications. Molecular and Cellular Proteomics. Sep. 26, 2002. vol. 1, No. 10, pp. 791-804.*
Lee et al. Applications of affinity chromatography in proteomics. Analytical Biochemistry. 2004. vol. 324, pp. 1-10.*
Blitzer et al. A Purified Serum Glycopeptide from Controls and Cystic Fibrosis Patients. I. Comparison of their Mucociliary Activity on Rabbit Tracheal Explants. Pediatr. Res. 1982. vol. 16, pp. 203-208.*
Blitzer et al. A Purified Serum Glycopeptide from Controls and Cystic Fibrosis Patients. III. The Association of the Ciliary Dyskinetic Activity with the Oligosaccharide Component. Pediatr. Res. 1984, vol. 18, pp. 540-543.*

* cited by examiner

*Primary Examiner*—Cecilia Tsang
*Assistant Examiner*—Marcela M Cordero Garcia

(57) ABSTRACT

A method useful in the analysis of glycosylated proteins, in which a mixture containing glycosylated proteins and unglycosylated proteins is contacted with a resin that includes a nucleophile bound to a solid support via a linker. The contacting is performed under conditions sufficient to result in removal of the glycosyl group from the glycosylated proteins and to concomitantly result in the deglycosylated proteins covalently bound to the solid support. The deglycosylated proteins bound to the solid support may be rinsed to remove proteins that are not covalently bound to the solid support. The deglycosylated proteins are released from the solid support and may be subjected to further purification and/or analysis.

22 Claims, No Drawings

ENRICHMENT AND TAGGING OF GLYCOSYLATED PROTEINS

FIELD OF THE INVENTION

The invention relates generally to analysis of proteins and peptides. More specifically, the invention relates to solid phase methods for enrichment of glycosylated proteins and/or peptides. Such methods are useful for preparing the glycosylated proteins and/or peptides for further analysis.

BACKGROUND OF THE INVENTION

Sequencing of the human genome, and the genomes of other species, has emphasized the fact that the expression and properties of a protein are often dependent on posttranslational modifications and, thus, cannot be predicted from the DNA sequence. This realization has spurred an interest in proteomics, the study of protein expression within a cell under defined conditions.

Traditionally, proteins from biological samples have been isolated and identified by separating the proteins using 2-D gel electrophoresis followed by identification of the protein using mass spectrometry. However, this method is time consuming and can only detect proteins that are highly abundant in the biological sample. Severe streaking causes deterioration in resolution of the electrophoretic separation when high loading is used in an attempt to visualize less abundant proteins.

Particular difficulties have been encountered in attempts to use 2-D gel electrophoresis/mass spectrometry to study glycosylated proteins, as they are often present in low abundance. Glycosylated proteins are of particular interest in proteomic studies, however, as such proteins often participate in signal transduction and other cellular processes.

Glycosylated proteins and peptides (also referred to herein as glycoproteins and glycopeptides, respectively) are normally isolated from mixtures using different lectin affinity columns. For example, a BS-II (*Bandeiraia simplicifolia*) column has a high specificity for peptides having O-linked N-acetyl glucosamine (O-GlcNAc) moieties. See Apffel et al. (1996) J. Chromatogr. A 732: 27-42. Geng et al. have reported using lectin affinity column chromatography to recover glycopeptides, followed by isotope tagging of the glycopeptides with generic N-terminal labels. See Geng et al. (2000) J. Chromatogr. A 870: 295-313.

Alternatively, the selective and sequential use of enzymes can cleave sugars, and the before and after results can be analysed, for example, by tandem mass spectrometry. See Geng et al. (2001) J. Chromatogr. B 752: 293-306. O-linked glycopeptides can be deglycosylated using O-glycosidase.

The mapping of O-GlcNAc sites after beta-elimination has been reported by Wells et al. See Wells et al. (2002) Molec. & Cell. Proteomics, 1.10, 791-804. After the beta-elimination reaction, Wells et al. used solution phase Michael-addition chemistry to label glycosylation sites of proteins with either dithiothreitol or biotin pentylamine and analyzed the products using mass spectrometry. The methods described by Wells et al. involved multiple purification and clean-up steps to provide the ultimate product.

While the above methods have greatly facilitated the study of glycoproteins, they have various disadvantages, such as requiring multiple purification or clean-up steps in isolating or labeling a target protein or collection of proteins. Thus, a method that does not suffer from the disadvantages of the above methods is desirable.

SUMMARY OF THE INVENTION

The invention addresses the aforementioned deficiencies in the art, and provides novel solid phase methods for separation of glycosylated proteins from a mixture containing glycosylated proteins and unglycosylated proteins. The separated proteins may then be subjected to further purification and/or analysis.

According to the invention, a mixture containing glycosylated proteins and unglycosylated proteins is contacted with a resin, wherein the resin typically comprises a nucleophile bound to a solid support via a linker. The contacting is performed under conditions sufficient to result in removal of the glycosyl group from the glycosylated proteins to yield deglycosylated proteins, said contacting resulting in the solid support covalently bound to the deglycosylated proteins. The deglycosylated proteins bound to the solid support may be rinsed to remove proteins that are not covalently bound to the solid support. The deglycosylated proteins are released from the solid support and may be subjected to further purification and/or analysis.

In an embodiment in accordance with the invention, prior to contacting the mixture containing glycosylated proteins and unglycosylated proteins with the resin, the mixture is treated to remove phosphate groups present on the proteins. In another embodiment in accordance with the invention, the mixture containing glycosylated and unglycosylated proteins is reacted with a reagent for protecting amine groups prior to contacting the mixture with the resin.

In certain embodiments, the mixture is contacted with the resin under conditions resulting in beta-elimination of the glycosyl groups from the glycosylated proteins to result in removal of the glycosyl groups from the glycosylated proteins to yield deglycosylated proteins, each deglycosylated protein having a deglycosylation site, the deglycosylated proteins bound to the solid support via their respective deglycosylation sites. In some embodiments, after rinsing the deglycoslated proteins bound to the solid support and release of the deglycosylated proteins from the solid support, the deglycosylated proteins are recovered and may be subjected to further purification and/or analysis.

In particular embodiments, the deglycosylated proteins are labeled with a tag as a result of the method. In such embodiments, the mixture containing glycosylated proteins and unglycosylated proteins is contacted with a resin that comprises a nucleophile bound to a solid support via a linker that includes a tag; the contacting results in the deglycosylated proteins bound to the solid support via the linker. In such embodiments, upon release of the deglycosylated protein, the portion of the linker that is the tag remains bound to the deglycosylated protein.

The present invention also provides a kit for separating glycosylated proteins from a mixture comprising glycosylated proteins and unglycosylated proteins according to the method of the invention. The kit comprises a resin, wherein the resin comprises a nucleophile covalently bound to a solid support via linker, wherein the linker comprises a tag, wherein the nucleophile is capable of reacting to covalently bind to a deglycosylated protein as described herein. The kit may further include an amine protecting group reagent and/or a dephosphorylating reagent. The resin provided in the kit preferably comprises a tag capable of remaining bound to the protein under conditions in which the bond between the tag and the solid support is labile.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "a solid support" includes a plurality of solid supports. In this specification and in the claims that follow, reference will be made to a number of terms that shall be defined to have the following meanings unless a contrary intention is apparent.

As used herein, "protein" references a compound having a series of amino acid subunits bound via peptide bonds; the protein may have from 2 to 1000 or more amino acid subunits. "Peptide" references a compound having a series of amino acid subunits bound via peptide bonds, wherein the compound has from about 2 to about 50 amino acid subunits, more typically from about 2 to about 30 amino acid subunits, still more typically from about 3 to about 20 amino acid subunits. "Amino acid" references an amphoteric compound containing an amino group and a carboxylic acid group; typical examples include the alpha amino acids that typically make up proteins. "Glycosylated protein" references a compound having a glycosyl group covalently bound to a protein. "Glycosyl group" refers to the monosaccharide or oligosaccharide group of a glycosylated protein. "Glycosylation site" references the site of attachment of the glycosyl group on the protein. "Unglycosylated protein" references a protein that does not have a glycosyl group associated with the protein. "Deglycosylated protein" references a protein that has had a glycosyl group removed from the protein, i.e. a protein that was at one time a glycosylated protein that has undergone removal of the glycosyl group. "Deglycosylation site" references the site from which the glycosyl group was removed from the protein.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). "Residue" is sometimes used herein to reference a moiety that is a subunit of a larger moiety having a plurality of the subunits joined together.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. As used herein with reference to the deglycosylated protein covalently bound to the solid support, "covalently bound" means that the deglycosylated protein is bonded to the immediately adjacent group (via which the deglycosylated protein is bound to the solid support) by a covalent bond, the covalent bond formed during the contacting of the mixture with the resin as described in greater detail herein.

By "protecting group" as used herein is meant a moiety which prevents a portion of a molecule from undergoing a chemical reaction under specified conditions, but which is removable from the molecule following exposure of the molecule to the specified conditions; the protecting group thus allows an unprotected portion of a molecule to undergo a chemical reaction under the specified conditions while preventing the protected portion of the molecule from undergoing a chemical reaction. This is in contrast to a "capping group," which permanently binds to a segment of a molecule to prevent any further chemical transformation of that segment. As used herein, an "amine protecting group" is a group used (or intended to be used) as a protecting group to protect an amine group as described in greater detail elsewhere herein.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, modified alkyl, and modified lower alkyl.

A "group" may include substituted and unsubstituted forms, where context permits. Typical substituents include one or more lower alkyl, modified alkyl, any halogen, hydroxy, or aryl. Any substituents are typically chosen so as not to substantially adversely affect reaction yield (for example, not lower it by more than 20% (or 10%, or 5% or 1%) of the yield otherwise obtained without a particular substituent or substituent combination).

The term "halo" or "halogen" is used in its conventional sense to refer to a chloro, bromo, fluoro or iodo substituent.

The term "alkyl" as used herein, unless otherwise specified, refers to a saturated straight chain, branched or cyclic hydrocarbon group of 1 to 24, typically 1 to 12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl. An alkyl group may be substituted or unsubstituted.

The term "modified alkyl" refers to an alkyl group having from 1 to 24 carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to an alkyl group having from one to six carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azido, carboxy, sulfide, sulfone, sulfoxy, phosphoryl, silyl, silyloxy, and boronyl. In particular embodiments, a modified alkyl group may include from one to about three substituents.

The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above. A haloalkyl group refers to an alkyl group that is substituted with one or more halogen atoms.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, modified lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)$_j$—Ar wherein j is an integer in the range of 1 to 24, more typically 1 to 6, and Ar is a monocyclic aryl moiety.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen, and the quaternized form of nitrogen. The term "sulfur heteroatoms" includes any oxidized form of sulfur. Examples of heterocyclic groups include purine, pyrimidine, piperidinyl, morpholinyl and pyrrolidinyl. Heterocylic groups may be substituted or unsubstituted.

The term "heteroaryl," as used herein, means an aromatic heterocycle which contains 1, 2, 3 or 4 heteroatoms selected from nitrogen, sulfur or oxygen. A heteroaryl may be fused to one or two rings, such as a cycloalkyl, a heterocycloalkyl, an aryl, or a heteroaryl. The point of attachment of a heteroaryl to a molecule may be on the heteroaryl, cycloalkyl, heterocycloalkyl or aryl ring, and the heteroaryl group may be attached through carbon or a heteroatom. Suitable heteroaryl groups include imidazolyl, furyl, pyrrolyl, thienyl, oxazolyl, thiazolyl, isoxazolyl, thiadiazolyl, oxadiazolyl, pyridinyl, pyrimidyl, pyrazinyl, pyridazinyl, quinolyl, isoquniolyl, indazolyl, benzoxazolyl, benzofuryl, benzothiazolyl, indolizinyl, imidazopyridinyl, pyrazolyl, triazolyl, isothiazolyl, oxazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl each of which is optionally substituted. Heteroaryl groups may be substituted or unsubstituted.

A heterocycloalkyl refers to a non-aromatic ring which contains one or more oxygen, nitrogen or sulfur (e.g., morpholine, piperidine, piperazine, pyrrolidine, and thiomorpholine). Heterocycloalkyl groups may be substituted or unsubstituted.

A primary amine group has the formula —NH$_2$. A secondary amine group is a group having the formula —NHR, wherein R is an alkyl group, a modified alkyl group, or an aromatic group.

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown.

Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. glycosyl or glycosyl-, yet further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. the indicated group may have a substituent; further e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

The methods described herein may find use in analyzing glycosylated proteins, which may indicate particular aspects of cell growth, such as disease state, state of differentiation, signal transduction, etc. However, many glycosylated proteins of interest are present in low abundance so that their presence is overwhelmed by other more abundant proteins and can go undetected by traditional methods of profiling cellular proteins. Separation of the glycosylated proteins from the unglycosylated proteins allows less abundant glycosylated proteins to be analysed with reduced (or eliminated) interference from the unglycosylated proteins.

The present invention provides a system for enriching glycosylated proteins from a mixture of glycosylated and unglycosylated proteins, such as a biological sample. Once unglycosylated proteins are removed from the mixture, glycosylated proteins that are present in low abundance are more readily detectable. A method in accordance with the present invention involves contacting the mixture of glycosylated and unglycosylated proteins with a resin, wherein the resin comprises a nucleophile bound to a solid support via a linker. Typically, the contacting is performed under conditions sufficient to remove the glycosyl group from the glycosylated protein to yield a deglycosylated protein having a deglycosylation site, the deglycosylated protein covalently bound to the solid support via the deglycosylation site. The deglycosylated protein covalently bound to the solid support may be rigorously washed to remove noncovalently bound molecules, e.g. unglycosylated proteins. The deglycosylated protein is released from the solid support and recovered, and typically further purified and/or subjected to analysis.

In an embodiment, a method in accordance with the present invention involves contacting a mixture of glycosylated and unglycosylated proteins with a resin, wherein the resin comprises a nucleophile bound to a solid support via a linker. Typically, the contacting is performed under conditions resulting in beta-elimination of the glycosyl groups from the glycosylated proteins, thus resulting in formation of unsaturated intermediates, each unsaturated intermediate having an unsaturated bond at the site of the elimination of the glycosyl group. The nucleophile of the resin will react with the unsaturated intermediate at the site of the unsaturated bond to result in the solid support covalently bound to the deglycosylated protein. After the deglycosylated proteins are covalently bound to the resin, they can be rigorously washed to remove noncovalently bound molecules, e.g. unglycosylated proteins, thereby improving the purity of the deglycosylated proteins.

Without limiting the scope of the invention to any particular mechanism, it is believed that SCHEME (A) describes reactions occurring in typical embodiments in accordance the invention. Upon contacting the mixture with the resin under the conditions described herein, the unsaturated intermediate is provided according to reaction (Ia), and reaction (Ib) shows the concomitant reaction of the resin with the unsaturated intermediate to result in the deglycosylated protein covalently bound to the solid support. Reaction (II) of SCHEME (A) shows the removal (e.g. by rinsing and filtration) of unglycosylated proteins from the deglycosylated protein bound to the solid support. Reaction (III) shows a typical embodiment in which the deglycosylated protein is released from the solid support to yield the deglycosylated protein to which a tag is attached.

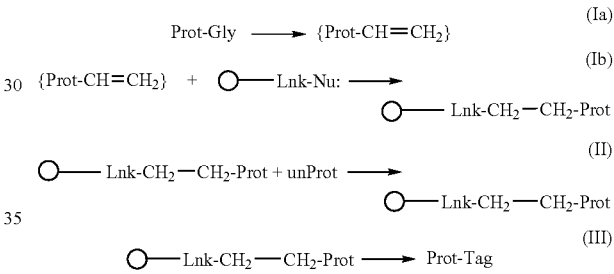

wherein:
Prot-Gly represents a glycosylated protein; Prot represents a protein; Gly represents a glycosyl group;
{Prot-CH=CH$_2$} represents an unsaturated intermediate;

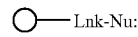

represents the resin having a nucleophile covalently bound to a solid support via a linker;

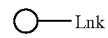

represents the solid support having the linker bound thereto;
Nu: represents the nucleophile;

represents the deglycosylated protein covalently bound to the solid support via the linker;
unProt represents unglycosylated protein; and
Prot-Tag represents protein having a tag released from the solid support.

The reactions (Ia) and (Ib) are conducted under conditions suitable for beta-elimination to occur to result in the unsaturated intermediate depicted in curly braces in equation (Ia). The curly braces are used to indicate that the unsaturated intermediate is formed in situ with the resin, such that the nucleophile concomitantly reacts with the unsaturated intermediate to form a covalent bond linking the deglycosylated protein to the solid support, as shown in reaction (Ib).

The resin comprises a nucleophile bound to a solid support via a linker. The solid support may comprise any suitable material adapted for its intended use in the methods described herein. The solid support should be essentially inert to the conditions of reactions used herein. In typical embodiments, the solid support is a rigid or semirigid material, such as beads, pallets, disks, capillaries, hollow fibers, needles, membrane (e.g., porous membranes which allow fluid to flow therethrough), sheets, solid fibers, cellulose beads, pore-glass beads, silica gels, polystyrene beads optionally cross-linked with divinylbenzene, grafted co-polymer beads, poly-acrylamide beads, latex beads, dimethylacrylamide beads optionally cross-linked with N,N'-bis-acryloyl ethylene diamine, glass particles coated with a hydrophobic polymer, or the like. Suitable solid supports are available from a variety of commercial sources including Sigma-Aldrich, NovaBiochem, and Beckman-Coulter, or may be synthesized using known techniques. In one embodiment, the solid support is magnetic, such as a magnetic particle. Magnetic particles suitable for use in the present invention are described in U.S. Pat. No. 6,551,843, the entire teachings of which are incorporated herein by reference.

In certain embodiments, the solid support has a surface and a modification layer disposed on (or bound to, directly or indirectly) the surface of the solid support. In such embodiments, the linker is bound to (directly or indirectly) the modification layer. Such modification layer may be formed on the surface of the substrate by methods known in the art of modifying supports to provide desired surface properties. In certain embodiments, the modification layer may be, e.g. a coating, a material deposited by deposition techniques known in the art, a hydrophobic layer, or a hydrophilic layer. In particular embodiments, the modification layer comprises a silane group to which the linker group is bound, directly or indirectly, e.g. via any linking group effective to link the linker to the silane group and stable to the conditions used in the methods herein.

In particular embodiments, resins in accordance with the present invention may be made using silane modified supports. A functional group attached (directly or indirectly, e.g. via a linking group) to the silane group on the support provides a site for further attachment to the support to occur. The support bearing the functional group is then contacted with a composition having a surface-binding group attached to a linker. The surface-binding group is capable of reacting with the functional group attached to the support to result in attachment of the linker to the solid support. Of course, other moieties, such as a nucleophile, attached to the linker group will thusly also be attached to the solid support. Alternatively, the nucleophile may be attached to the linker after the linker is already bound to the solid support. The resulting resin may then be used in the methods described herein. The functional group attached to the substrate will typically be selected from amine, hydroxyl, sulfhydryl, carboxyl, carbonyl, phosphate and thiophosphate, and combinations thereof. The surface-binding group comprises a group that is chemically reactive with (and forms a covalent bond with) the functional group attached to the substrate. The surface-binding group will typically be selected from succinimidyl ester, isothiocyanate, isocyanate, haloacetamide, dichlorotriazine, maleimide, sulphonyl halide, alkylimidoester, arylimidoester, substituted hydrazine, substituted hydroxylamine, carbodiimide, acyl halide, anhydride, phosphoramidite, acrylate and acrylamide. Selection of an appropriate surface-binding group will be based on the identity of the functional group attached to the substrate, and vice versa. Such selection is within the skill of those in the art given the disclosure herein.

The linker is a linking group via which the solid support is bound to the nucleophile. The linker comprises a cleavable group and an optional tag, wherein the cleavable group is covalently bound to the optional tag. The resin comprises, in order, the following: the solid substrate, the cleavable group, the tag (if present), and the nucleophile. The nucleophile is bound to the solid support via the cleavable group. The cleavable group is any group that is unreactive to the conditions of the other reactions used in the method of the invention, but which may be cleaved to release the deglycosylated protein from the solid substrate in accordance with the method of the present invention. Thus, the cleavable group is selected to be stable under the conditions under which the resin is contacted with the mixture of glycosylated proteins and unglycosylated proteins, but to be labile under the conditions used for release of the deglycosylated protein from the solid support. Orthogonal chemistries employing cleavable groups that are stable under specified conditions and labile under other specified conditions are known in the art. The cleavable group may be selected from, for example, groups that are labile upon exposure to UV light (photolabile groups), groups that are labile upon exposure to acid, groups that are labile upon exposure to base, groups that are labile upon exposure to hydrides or organo-metallic reagents, or groups that are labile upon exposure to oxidative reagents. Certain materials, e.g. functionalized supports, that may be modified to provide resins in accordance with the present invention are available commercially. One example is photocleavable resins which are supplied with cleavable groups already bound to the solid support, such as are supplied by (EMD Biosciences, Inc., San Diego, Calif.). A cleavable group that is photolabile and which may be incorporated in the linker is shown in structure (IV)

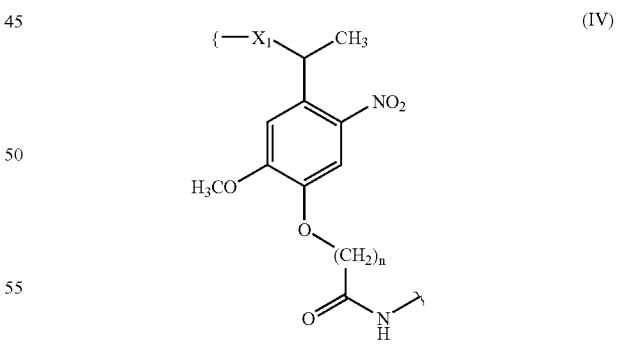

wherein:

n is an integer in the range from 1 to about 25, and $X_1$ is —O— or —NH—; and wherein the nucleophile is attached to the cleavable group via the $X_1$ and the cleavable group is attached to the solid support via the —NH—} shown in structure (IV).

Other examples of suitable cleavable groups include N-methoxy β-alanine, benzotriazoles, hydrazinobenzamides, aminoxanthenes, phenyl-aminomethyl-benzenes (A specific example of a commercial reagent=9-fmoc-aminoxanthen-3yloxy-Merrifield resin. See also Brown, Contemporary Organic Synthesis (1997) 4(3):216-237.

The cleavable group may be substituted or unsubstituted. The linker may be bound to the solid support via any available group of the cleavable group, such as any substituent of the cleavable group (e.g. a modified alkyl group bound to the cleavable group, the cleavable group bound to the substrate via the modified alkyl group).

The linker may further comprise a tag bound to the solid support via the cleavable group. In embodiments including the tag, the nucleophile is bound to the cleavable group via the tag. The tag may be any group that is intended to be bound to the deglycosylated protein after release of the deglycosylated protein from the solid support. The tag typically imparts a particular observable property to the tagged protein, for example, an altered mass, and altered optical property, or an altered chemical activity, wherein the observable property is typically observed after release of the tagged, deglycosylated protein from the solid support. The tag should be stable to the conditions of use of the resin as disclosed herein. In certain embodiments, the tag is selected from an isotope labeled tag, a mass tag, a fluorescent tag, an affinity tag, or a chemical group having a specific reactivity (e.g. capable of undergoing a specific reaction under appropriate conditions). In some embodiments, the tag may comprise one or more groups selected from an alkyl group, a modified alkyl group, an aryl group, an amino acid, a peptide, or a fluorophore. In particular embodiments, the tag is labeled with an isotopically stable isotope by substituting an isotopically stable isotope, such as $^2H$, $^{13}C$, $^{15}N$, $^{17}O$, $^{18}O$, or $^{34}S$, for one or more of the atoms in the tag. In a particular embodiment, the tagging group is labeled with one or more deuterium ($^2H$). In some embodiments, the tag is an affinity tag that comprises a moiety that is capable of specifically binding or forming a complex with a corresponding molecular entity; in some examples the tag may comprise an antigen, a biotin, or a carbohydrate, wherein the corresponding molecular entity would be an antibody (or antibody fragment), an avidin (or streptavidin), or a lectin, respectively. Other typical tag-antitag pairs for use in affinity applications are known in the art. In some embodiments, the tag may comprise a functional group that is capable of specifically reacting with a corresponding reactive group to form a covalent bond, e.g. to provide a covalent attachment to another moiety. The selection of the functional group/reactive group will depend on the intended use of the groups and is within the skill in the art given the disclosure herein.

In embodiments in which a tag is included in the linker, the tag is transferred to (and remains bound to) the deglycosylated protein upon release of the deglycosylated protein from the solid support. For example, in embodiments in which a solid support is bound to a deglycosylated protein via a linker that includes a tag that is isotope labeled, the isotope label will be transferred to the deglycosylated protein and thereby isotope labels the deglycosylated proteins in the mixture.

The nucleophile, as referenced herein, is a reactive group that has an available electron pair with which it attacks another atom to form a new covalent bond. The nucleophile bound to the solid support as described herein, in the presence of the mixture of glycosylated and unglycosylated proteins, is capable of reacting under conditions conducive to beta-elimination to result in the deglycosylated protein bound to the solid support. Under conditions of beta elimination of the glycosyl group from a glycosylated protein, an unsaturated intermediate is formed (typically a dehydro-amino acid residue, e.g. dehydroserine or dehydrothreonine). The nucleophile is capable of reacting (by attacking the unsaturated bond on the unsaturated intermediate generated in the β-elimination reaction) to provide the deglycosylated protein bound to the solid substrate via the linker. The resin comprises the nucleophile attached to the solid substrate via the linker such that the nucleophile is accessible to molecules in solution, e.g. the unsaturated intermediate, when the resin is contacted with the mixture of glycosylated proteins and unglycosylated proteins.

Typical nucleophiles include thiol groups, amine groups, and hydroxyl groups, and any other nucleophilic group capable of reacting as described herein to covalently bind the deglycosylated protein to the solid support. The nucleophile can react with the beta-elimination product (the unsaturated intermediate) to result in the deglycosylated protein covalently bound to the solid support. In one embodiment, the resin has primary or secondary amine groups that serve as the nucleophile. In another embodiment, the resin has any other nucleophile that can react to result in the deglycosylated protein covalently bound to the solid support.

A glycosylated protein in the mixture of glycosylated proteins and unglycosylated proteins typically comprises at least one glycosyl group bound to a protein. The glycosyl group is typically attached to the protein via a serine or threonine side chain, as is generally known in the art. The glycosyl group may be a monosaccharide or may be an oligosaccharide. The glycosyl group typically comprises one or more saccharide monomer subunits, in which the saccharide monomer subunits typically are selected from N-acetyl glucosamine, mannose, and muramic acid, sialic acids, N-acetyl galactosamine, although other saccharide monomer subunits known in the literature of glycosylated proteins may be present. In particular embodiments, the glycosylated proteins comprise O-linked sugar residues, such as O-linked N-acetyl glucosamine. The glycosyl group is susceptible to beta-elimination from the protein to which it is bound under the conditions under which the mixture is contacted with the resin.

The mixture may include one or more glycosylated proteins and other substances, including unglycosylated proteins and other materials such as may be found in biological samples. A biological sample is a sample obtained from a biological source. The mixture of glycosylated proteins and unglycosylated proteins may be obtained by a process including obtaining a biological sample and optionally subjecting the biological sample to one or more separation processes. In one embodiment, the proteins in the mixture are digested with one or more proteases before contacting the mixture with the resin. In this embodiment, glycosylated or unglycosylated proteins in the mixture have a molecular weight of about 5000 daltons or less after digestion. In typical embodiments, prior to contacting the mixture with the resin, the mixture may be treated to dephosphorylate the proteins in the mixture, e.g. by treating the mixture with a phosphatase to remove phosphate moieties from the proteins. Conditions and protocols for performing the dephosphorylation are known in the art.

In a preferred embodiment, the amine groups of glycosylated proteins and unglycosylated proteins in a mixture may be protected with an amine protecting group before contacting the mixture with the resin. The selection of a suitable amine protecting group depends upon the conditions to which the protecting group is being exposed and to other functional groups which may be present in the protein molecule. Suitable amine protecting groups and reagents for protecting amines are described in Greene and Wuts, "Protective Groups in Organic Synthesis", John Wiley & Sons (1991), the entire teachings of which are incorporated into this application by reference. The skilled artisan can select, using no more than routine experimentation, suitable protecting groups for use in the disclosed method, including amine protecting groups other than those described below, as well as conditions for applying and removing the protecting groups to regenerate the amine group. Examples of suitable amine protecting groups include benzyloxycarbonyl, tert-butoxycarbonyl (BOC), tert-butyl, benzyl and fluorenylmethyloxycarbonyl (Fmoc).

In typical embodiments, the contacting of the mixture with the resin is performed under conditions conducive to beta-elimination of the glycosyl group from the glycosylated protein such that the unsaturated intermediate is generated in situ with the resin. The further reaction of the nucleophile of the resin with the unsaturated intermediate is concomitant and typically does not require any further steps, such as any further separations, change of conditions, or the like, to provide the product having the deglycosylated protein covalently bound to the solid support.

Typically, the conditions under which the mixture is contacted with the resin include addition of a base for a time sufficient to result in beta-elimination of glycosyl groups from the glycosylated proteins in the mixture, although any other suitable conditions resulting in the deglycosylated proteins covalently bound to the solid support may be used. The conditions for beta-elimination typically include the addition of a base at a sufficient concentration and for a time sufficient to result in elimination of the glycosyl group. The conditions are typically those reported in the examples herein and as reported in Wells et al. (2002) Molec. & Cell. Proteomics, 1.10, 791-804. The conditions used will also vary depending on the identity of the nucleophile; establishing conditions effective with the selected nucleophile is in the capability of those skilled in the art given the disclosure herein. In an embodiment, the resin is contacted with the mixture under aqueous conditions in the presence of a source of hydroxide ion.

The solid support having the deglycosylated protein covalently bound thereto is typically washed to remove unglycosylated proteins from the deglycoylated protein bound to the solid support. This may be performed using any effective washing protocol, e.g. rinsing the solid support with an appropriate solution (e.g. a solvent or a buffer) capable of stripping the unglycosylated proteins from the solid support. In an embodiment, the resin is washed with a solution containing a high salt concentration (e.g., at least about 0.1 M salt). Selection of an appropriate solvent or buffer is within ordinary skill in the art. Typical examples include: aqueous alcohol, aqueous acetonitrile, methanol or DMF (dimethyl formamide). The wash solution may be separated from the solid supports in any effective manner, e.g. filtration, and is within ordinary skill in the art.

The deglycosylated protein is released from the solid support by cleaving a bond between the solid support and the deglycosylated protein. For example, the deglycosylated protein is bound to the solid support via a linker that includes a cleavable group wherein the cleavable group is labile under specific conditions corresponding to the cleavable group. In certain embodiments, the cleavable group is a photolabile group, and the conditions for releasing the deglycosylated protein include exposing the solid support having deglycosylated protein covalently bound thereto to light of the appropriate wavelength (e.g. UV light) for cleaving the photolabile cleavable group. In certain embodiments, the cleavable group may be acid labile, in which case it can be cleaved by contacting the solid support having deglycosylated protein covalently bound thereto with an aqueous acid solution, such as an aqueous solution of trifluoroacetic acid. In an embodiment, the amine groups of the glycosylated proteins are protected with an acid labile amine protecting group, such as 2-(t-butoxycarbonyloxy-imino)2-phenylacetonitrile (BOC-ON, available from Aldrich, Milwaukee, Wis.), prior to contacting the mixture with the resin. In this embodiment, the amine protecting groups may be cleaved simultaneously with cleavage of an acid labile cleavable group of the linker between the solid support and the deglycosylated protein by, for example, contacting the solid support having deglycosylated proteins covalently bound thereto with a concentrated solution of trifluoroacetic acid (e.g., 90% trifluoroacetic acid in 10% water). Other embodiments may leave the amine-protecting groups intact, while cleaving the deglycosylated protein from the solid support.

After the deglycosylated protein is released from the solid support, the deglycosylated protein may be subjected to further purification and/or analysis. Such further purification and/or analysis may include mass spectrometry, HPLC, fluorimetric analysis, gel electrophoresis, or any other purification and/or analysis.

The invention also includes a kit for analysing glycosylated proteins from a mixture comprising glycosylated proteins and unglycosylated proteins. In one embodiment, the kit includes a resin having a nucleophile bound to a solid support via a linker, wherein the nucleophile is capable of reacting with a glycosylated protein under conditions conducive to beta-elimination of the gylcosyl group to result in deglycosylation of the glycosylated protein and concomitant formation of a covalent bond bonding the deglycosylated protein to the solid support. The resin is included in a package, wherein the package may also include one or more additional items, such as reagents for use in preparing the resin for use or for using the resin, (such as a solution effective to release the deglycosylated protein from the resin), one or more filters for use with the resin, an/or reagents for preparing the mixture of proteins (e.g. a phosphatase for removing phosphate groups, a protease for digesting proteins in the mixture). In one embodiment, the kit also includes a reagent for protecting amine groups, such as BOC—ON, benzyloxycarbonyl chloride, acetyl chloride, benzyloxycarbonyl bromide, tert-butyl chloride, tert-butyl bromide, benzyl chloride, benzyl bromide, fluorenylmethyloxycarbonyl chloride, and fluorenylmethyloxycarbonyl bromide. In an embodiment, the resin included in the kit has a linker that comprises tag, such as an isotope labeled linker, an isotope labeled amino acid, or an isotope labeled peptide that can bind to proteins in the protein mixture.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Preparation of the Resin

First, the resin comprising the nucleophile bound to the solid support via a linker is prepared. In this example, a β-alanine group is bound to a support such that the primary amino is available to serve as the nucleophile. The Sieber Amide Resin is commercially available in a bead format that provides a support having an acid-labile cleavable group attached to a solid support. Alternatively, a resin with a photolabile cleavable group is commercially available in a bead format (EMD Biosciences, Inc., San Diego, Calif.) and may be used (with appropriate modifications to the experimental protocol) in place of the Sieber Amid Resin described herein.

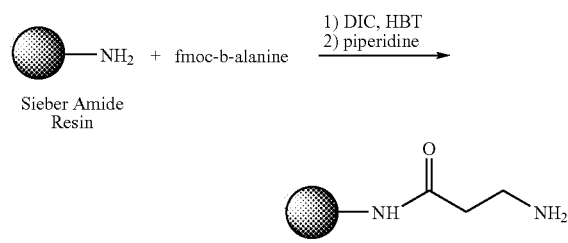

Fmoc-Seiber Amide Resin beads (Calbiochem #01-64-0059) are prepared for coupling to β-alanine in the following way: At least an equimolar or greater amount of the Fmoc-Seiber Amide Resin beads (0.25-0.6 mmol amines/g) is deprotected by placing the Fmoc-Seiber Amide Resin beads into a 20% solution of piperdine in anhydrous DMF. This is shaken at room temperature for 30 minutes. The resulting deprotected beads are then filtered and rinsed with DMF. A combined solution of equimolar amounts of 1-hydroxybenzotriazole ("HBT"), fmoc-β-alanine (Calbiochem #04-12-1044) and diisopropylcarbodiimide ("DIC") is placed with the deprotected beads in a small amount of dry DMF. This mixture is shaken at room temperature for 90 min. The beads are again filtered and washed with DMF, then methylene chloride. A final capping step is performed by placing the beads into methylene chloride containing 2 ml of 40% acetic anhydride/60% pyridine for 30 min. The beads are again filtered and washed with DMF.

(For preparation of heavy isotope tag, substitute β-alanine-$^{13}C_3$, $^{15}N$ (Isotec #49-082-2) for β-alanine in the above procedure. The fmoc derivative of this compound is prepared according to standard procedures.)

The fmoc protecting group on the β-alanine is removed by placing the beads into 20% solution of piperdine in anhydrous DMF for 30 minutes. Filter the beads and rinse with DMF.

It is noted that other amino acids may be substituted for the β-alanine, and in particular, an amino acid having a free thiol or hydroxyl group may be used where the free thiol or hydroxyl acts as the nucleophile.

Digestion-Phosphatase Treatment of Protein Samples

Proteins are suspended in 40 mM ammonium bicarbonate and digested with trypsin overnight at 37° C. according to typical digestion protocols known in the art. The resulting digested proteins are dried down and resuspended in 40 mM ammonium bicarbonate and 1 mM magnesium chloride. Alkaline phosphatase is added and the resulting proteins are incubated at 37° C. for 4 hours, then dried via a Thermo Savant SpeedVac™ evaporator.

Attaching Proteins to Beads

The dried down proteins are resuspended in 1% triethylamine, 0.1% NaOH, 20% ethanol in aqueous solution while an equimolar or slightly greater amount of the beads (prepared above) is added (the beads having either the isotopically light or heavy version of the β-alanine, depending on experimental design). The reaction is incubated at 50° C. for 2.5 hours and then quenched with trifluoroacetic acid. This reaction results in deglycosylation of the proteins and also results in the deglycosylated proteins bound to the beads. The beads are filtered away from the reaction mixture and washed with deionized water then DMF.

Cleavage of Tagged-Proteins from Bead

The beads are pre-swelled in dichloromethane in a sealable sintered glass funnel. Excess dichloromethane is then removed. Trifluoroacetic acid (1-2%) in dry dichloromethane is added to the funnel and the contents shaken for 2 minutes. The solution is filtered, e.g. by applying nitrogen pressure. The acid addition step is repeated 1-2 times more, and then the beads are rinsed with methanol. The filtrate is evaporated under reduced pressure to recover the deglycosylated proteins having an added β-alanine tag (optionally isotopically labeled). These products can be resuspended in water and subjected to LC-MS analysis.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method for separating a deglycosylated protein comprising
   a) obtaining a mixture comprising a glycosylated protein and unglycosylated proteins, wherein the glycosylated protein comprises a protein having an O linked glycosylation site and a glycosyl group bound to the protein via the glycosylation site and has a molecular weight of 5000 daltons or less,
   b) contacting the mixture with a resin, wherein the resin comprises a nucleophile bound to a solid support via a linker, wherein said nucleophile is selected from the group consisting of amine, hydroxyl, sulfhydryl, and combinations thereof, said contacting done under conditions sufficient to remove the glycosyl group by β-elimination from the glycosylated protein to yield the deglycosylated protein having an unsaturated intermediate at the deglycosylation site, the deglycosylated protein bound to the solid support via the unsaturated intermediate at the deglycosylation site;
   c) rinsing the bound deglycosylated protein, thereby removing unglycosylated proteins;
   d) releasing the deglycosylated protein from the solid support.

2. The method of claim 1 wherein the mixture comprises a plurality of glycosylated proteins.

3. The method of claim 1, further comprising dephosphorylating proteins of the mixture prior to contacting the mixture with the resin.

4. The method of claim 1, further comprising subjecting the released proteins to mass spectrometric analysis.

5. The method of claim 1, further comprising subjecting the released proteins to analysis by gel electrophoresis.

6. The method of claim 1, further comprising subjecting the released proteins to analysis by HPLC.

7. The method of claim 1, further comprising reacting proteins of the mixture with a reagent for protecting amine groups prior to contacting the mixture with the resin.

8. The method of claim 1, wherein the contacting is done under aqueous conditions in the presence of a source of hydroxide ion, said conditions resulting in β-elimination of the glycosyl group from the glycosylated protein to result in an unsaturated intermediate, said conditions sufficient to result in reaction of the nucleophile with the unsaturated intermediate to yield the deglycosylated protein having a deglycosylation site, the deglycosylated protein bound to the solid support via the deglycosylation site.

9. The method of claim 1, wherein the resin comprises an amino acid residue bound to the solid support, wherein the amino acid residue has a primary or secondary amine group, wherein the primary or secondary amine group is the nucleophile.

10. The method of claim 9, wherein the amino acid residue is isotope labeled, and wherein the isotope labeled amino acid residue remains bound to the deglycosylated protein when the deglycosylated protein is released from the solid support.

11. The method of claim 1, wherein the resin comprises an amino acid residue bound to the solid support, wherein the amino acid residue has a sulfhydryl group, wherein the sulfhydryl is the nucleophile.

12. The method of claim 11, wherein the amino acid residue is isotope labeled, and wherein the isotope labeled amino acid residue remains bound to the deglycosylated protein when the deglycosylated protein is released from the solid support.

13. The method of claim 1, wherein the resin comprises a peptide bound to the solid support, wherein the peptide has a primary or secondary amine group, wherein the primary or secondary amine group is the nucleophile.

14. The method of claim 13, wherein the peptide is isotope labeled, and wherein the isotope labeled peptide remains bound to the deglycosylated protein when the deglycosylated protein is released from the solid support.

15. The method of claim 1, wherein the linker comprises a tag, and wherein the tag remains bound to the deglycosylated protein when the deglycosylated protein is released from the solid support.

16. The method of claim 15, wherein the tag is selected from a mass tag, a fluorescent tag, an affinity tag, or a chemical group having a specific reactivity.

17. The method of claim 1, wherein the linker comprises a cleavable group which is stable under the conditions under which the resin is contacted with the mixture of glycosylated proteins and unglycosylated proteins, but which is labile under the conditions used for release of the deglycosylated protein from the solid support.

18. The method of claim 1, wherein the deglycosylated protein is released from the solid support by exposing the resin bound deglycosylated protein to light.

19. The method of claim 1, wherein the deglycosylated protein is released from the solid support by exposing the resin bound deglycosylated protein to acid.

20. The method of claim 1, wherein the deglycosylated protein is released from the solid support by exposing the resin bound deglycosylated protein to a hydride.

21. The method of claim 1, wherein the deglycosylated protein is released from the solid support by exposing the resin bound deglycosylated protein to an organometalic reagent.

22. The method of claim 1, wherein the deglycosylated protein is released from the solid support by exposing the resin bound deglycosylated protein to oxidative reagents.

* * * * *

UNITED STATES PATENT AND TRADEMARK OFFICE
CERTIFICATE OF CORRECTION

PATENT NO. : 7,384,754 B2  
APPLICATION NO. : 10/699449  
DATED : June 10, 2008  
INVENTOR(S) : Robotti Page 1 of 1

It is certified that error appears in the above-identified patent and that said Letters Patent is hereby corrected as shown below:

On the title page, item (56), under "Other Publications", in column 1, line 2, delete "anlysis" and insert -- analysis --, therefor.

On the title page, item (56), under "Other Publications", in column 2, line 7, delete "Thronine" and insert -- Threonine --, therefor.

Signed and Sealed this

Twenty-eighth Day of October, 2008

JON W. DUDAS  
*Director of the United States Patent and Trademark Office*